US005412126A

United States Patent [19]
King et al.

[11] Patent Number: 5,412,126
[45] Date of Patent: May 2, 1995

[54] CARBOXYLIC ACID SORPTION REGENERATION PROCESS

[75] Inventors: C. Judson King, Kensington, Calif.; Loree J. Poole, Baton Rouge, La.

[73] Assignee: The Regents of the University of California, Oakland, Calif.

[21] Appl. No.: 31,166

[22] Filed: Mar. 12, 1993

Related U.S. Application Data

[63] Continuation-in-part of Ser. No. 686,543, Apr. 17, 1991, abandoned.

[51] Int. Cl.6 .............................................. C11B 7/00
[52] U.S. Cl. .................................. 554/185; 554/184; 554/191; 554/193; 562/580; 562/584; 562/585
[58] Field of Search .................. 562/584, 580, 585; 554/185, 191, 184, 193

[56] References Cited

U.S. PATENT DOCUMENTS

| | | | |
|---|---|---|---|
| 4,275,234 | 6/1981 | Baniel et al. | 562/584 |
| 4,323,702 | 4/1982 | Kawabata et al. | 562/485 |
| 4,405,717 | 9/1983 | Urbas | 435/140 |
| 4,444,881 | 4/1984 | Urbas | 435/139 |
| 4,720,579 | 1/1988 | Kulprathipanja | 562/580 |
| 4,855,494 | 8/1989 | Margureanu et al. | 562/580 |
| 4,924,027 | 5/1990 | Kulprathipanja | 562/580 |

FOREIGN PATENT DOCUMENTS 2064526  6/1981  United Kingdom .

OTHER PUBLICATIONS

Poole et al, Ind. Eng. Chem. Res., vol. 30, 1991, 923–929.
Tamada et al., "Extraction of carboxylic acids with amine extracts. I–Equilibria and Law-of-Mass-Action modeling" *Ind. Eng. Chem. Res.* (1990) 29:1319–1326.
Tamada et al., "Extraction of carboxylic acids with amine extractants. II–Chemical interactions and interpretation of data" *Ind. Eng. Chem. Res.* (1990) 29:1327–1333.
Tamada et al., "Extraction of carboxylic acids with amine extractants. III–Effect of temperature, water extraction, and process consideration" *Ind. Eng. Chem. Res.* (1990) 29:1333–1338.
King, C. J. "Acetic acid extraction" *Solvent Extraction Handbook* Lo, T. C. et al., eds., Wiley–Interscience: New York, 1983. A title page and table of contents is provided herewith.
Holten, C. H., *Lactic Acid: Properties and Chemistry of Lactic Acid and Derivatives* Chapter IV, V, VI, VII, VIII, XI, 1983.
Pearson et al., (contribution from the Furman Chemical Laboratory), Vanderbilt University, pp. 1356–1360, 1983.
Steitweiser & Heathcock *Amide Formation* pp. 440, 438, 439, 477, 478, 1983.
Kaufman, R. G., *Chemistry* "The Thermal Decomposition of Trimethylamine" pp. 4082, 1983.
Michell, J. A., "The Preparation of Aliphatic Amides" (May 1931) pp. 1879–1883.
Lockwood, L. B., "Production of organic acids by fermentation" *Microbial Technology* Peppler, H., et al., eds., Academic Press, New York, (1979) pp. 356–387.
Busche, R. M., "The business of biomass" *Biotechnol. Prog.* (1985) 1:165–180.
Sato et al., "Fermentative production of succinic acid from n-paraffin by *Candida brumptii* IFO 0731" *Agr. Biol. Chem.* (1972) 36(11):1969–1974.
Lipinsky et al., "Is lactic acid a commodity chemical?" *Chemical Engineering Progress* (Aug. 1986) pp. 26–32.
Kuo et al., "Use of absorbents for recovery of acetic acid from aqueous solutions. I–Factors governing capacity" *Separ. & Purif. Methods* (1987) 16:31–64.
Poole et al., "Regeneration of carboxylic acid–amine extracts by back-extraction with an aqueous solution of a volatile amine" *Ind. Eng. Chem. Res.* (1991) 30(5):923–929.

*Primary Examiner*—José G. Dees
*Assistant Examiner*—Deborah D. Carr
*Attorney, Agent, or Firm*—Paul R. Martin

[57] ABSTRACT

Carboxylic acids are sorbed from aqueous feedstocks into an organic liquid phase or onto a solid adsorbent. The acids are freed from the sorbent phase by treating it with aqueous alkylamine thus forming an alkylammonium carboxylate which is dewatered and decomposed to the desired carboxylic acid and the alkylamine.

24 Claims, 7 Drawing Sheets

CARBOXYLIC ACID SORPTION REGENERATION PROCESS

ORIGIN OF THE INVENTION

This invention was made in the performance of work funded by the Energy Conservation and Utilization Technology (ECUT) Division and Advanced Industrial Concepts Division of the United States Department of Energy under Contract No. DE-AC03-76SFO0098. The United States Government has rights to this invention.

This is a continuation-in-part of U.S. Ser. No. 686,543 filed on Apr. 17, 1991, now abandoned.

TECHNICAL FIELD

The invention is in the field of chemical engineering. More particularly it relates to improvements in sorption (i.e. ion exchange and solvent) extraction processes for recovering carboxylic acids from aqueous streams.

BACKGROUND OF THE INVENTION

Carboxylic acids are important chemicals of commerce. They appear as desired or contaminating constituents of a wide range of aqueous process streams. Historically, they were produced from animal fat or vegetable oil sources or from petroleum sources in substantially nonaqueous systems. More recently, they have been identified among the most attractive products for manufacture from biomass (e.g., corn starch) by fermentation. In these more advanced processes, the carboxylic acid is generated as a dilute solution in an aqueous fermentation broth. Acetic acid is recovered commercially from dilute aqueous solutions by distillation or by extraction with solvents such as isopropyl acetate, other esters, or ethers. Aqueous solutions are created during the manufacture of adipic acid. Citric acid is recovered from fermentation broths commercially by solvent extraction with high-molecular-weight tertiary amines (e.g., tridecylamine) in a diluent composed of a hydrocarbon (e.g., kerosene) and an alcohol (e.g., n-decanol). Citric acid commands a substantial market, which is increasing as detergent manufacturers switch to citric acid as "builder". Lactic acid (raw material for biodegradable plastics), succinic acid, malic acid, fumaric acid, and other carboxylic acids which may be manufactured on a large scale by fermentation of biomass are creating considerable interest in solvent extraction as a means of recovery. Carboxylic acids are also stable oxidation products and frequently appear as by-products or contaminants in aqueous and organic waste streams.

There are numerous current and potential industrial and environmental applications where it is desirable to recover these and other carboxylic acids from aqueous solutions. Examples include the production of citric acid and other acids by fermentation (Lockwood, 1979; Busche, 1985) and removal and recovery of carboxylic acids from aqueous waste streams. (All references noted herein are listed below in a section of the specification entitled "References.") For volatile carboxylic acids, such as acetic, distillation and azeotropic or extractive distillation are alternatives, along with solvent extraction and adsorption (King, 1983; Kuo et al., 1987). For low-volatility carboxylic acids, e.g., dicarboxylic acids and hydroxycarboxylic acids, distillative processes are expensive and often cannot isolate the desired acid.

For acids such as citric and lactic, the classical approach for recovery from a fermentation broth has been to add calcium hydroxide to form the calcium salt of the carboxylic acid, to which an acid such as sulfuric is added to liberate the free carboxylic acid. This approach consumes chemicals (e.g., lime and sulfuric acid) and produces a waste salt stream. Consequently, this method is falling out of favor.

B. Urbas, in U.S. Pat. No. 4,405,717 and No. 4,444,881 teaches a process for recovering acetic acid, lactic acid, butyric acid and citric acid directly from fermentation broths. This process involves converting the acid to a calcium salt and then adding a tertiary amine carbonate (especially tributylamine carbonate) to give a trialkylammonium salt of the acid and calcium carbonate. The trialkylammonium carboxylate is heated to give the acid and the corresponding trialkylamine. This process has the disadvantage that it generates calcium carbonate, a solid waste that needs to be disposed of or heated to high temperatures in a kiln to convert it back to calcium oxide. Also in these patents, there is a preference for higher molecular weight amines and the use of distillation to remove volatile acids from the less volatile amines.

Solvent extraction is often effective for recovery of these low-volatility carboxylic acids from aqueous solution. Reactive, basic extractants, e.g., tertiary amines or phosphine oxides, can be used to gain greater solvent capacity and selectivity with respect to water and other species. A process developed by Miles, Inc. (Baniel et al., 1981) for recovery of citric acid from fermentation solutions uses a solvent composed of a tertiary amine extractant in a hydrocarbon diluent with an alcohol modifier. This extractant is regenerated by back-extraction of the acid into water at a higher temperature. Back-extraction following a shift in diluent composition, achieved, e.g., by distillation, is another possibility for regeneration, and can be combined with a swing of temperature (Tamada and King, 1990). The overall degree of concentration relative to the feed that can be achieved by these methods is limited by the extent to which the distribution equilibrium for the carboxylic acid can be changed between forward and back-extraction.

Ion exchange and adsorption have also been employed in carboxylic acid recovery schemes. U.S. Pat. No. 4,720,579 to Kulprathipanja discloses the use of styrene-divinylbenzene resins to adsorb citric acid with regeneration by water or by a mixture of acetone and water. Similarly, Great Britain Patent No. 2,064,526A discloses the use of adsorbents containing pyridyl functional groups combined with regeneration by leaching with an organic solvent such as an alcohol or a ketone. U.S. Pat. No. 4,924,027 to Kulprathipanja and Strong discloses adsorption of citric acid by adsorbents containing tertiary amine or pyridyl functionalities (including Bio-Rad AG3-X4A and AG4-X4), with regeneration using an aqueous solution of sodium, potassium or ammonium hydroxide, yielding the respective sodium, potassium or ammonium citrate. Treatment of these citrates with a strong acid would yield the free citric acid form. In each of these solutions the citric acid is adsorbed from an aqueous solution bekow the pKa of citric acid.

As can be seen from this description of background, various methods used heretofore to recover carboxylic acids have presented limitations and thus offer opportunities for improvement. It is accordingly a general object of the invention to provide an efficient process for the recovery of carboxylic acids from aqueous solutions which neither consumes large amounts of chemicals nor generates waste chemical streams.

REFERENCES

The following references are known to one or more of the present inventors and relate to the general subject matter of the present invention:

Baniel, A. M.; Blumberg, R.; Hajdu, K. "Recovery of Acids from Aqueous Solutions". U.S. Pat. No. 4,275,234. Jun. 23, 1981.

Busche, R. M. "The Business of Biomass". *Biotechnol. Progr.* 1985, 1, 165–180.

Cullis, C. F.; Waddington, D. J. "The Gaseous Oxidation of Tertiary Aliphatic Amines, II. Trimethylamine". *Proc. Royal Soc. A* 1958, 246, 91–98.

Great Britan Patent No. 2,064,526A and U.S. Pat. No. 4,323,702.

Holten, C. H. *Lactic Acid: Properties and Chemistry of Lactic Acid and Derivatives.* Verlag Chemie: Copenhagen, 1971.

Jones, P. W.; Gesser, H. D. "Formation of Hydrogen from Amine Oxidation and Pyrolysis". *Combustion and Flame* 1972, 19, 134.

Kaufman, R. G. "The Thermal Decomposition of Trimethylamine". Ph.D. dissertation, The Catholic University of America, Washington D.C., 1962.

King, C. J. "Acetic Acid Extraction". In *Solvent Extraction Handbook;* Lo, T. C.; Baird, M. H. I.; Hanson, C., Eds.; Wiley-Interscience: New York, 1983.

Kulprathipanja, U.S. Pat. No. 4,720,579.

Kulprathipanja and Strong, U.S. Pat. No. 4,924,027.

Kuo, Y.; Munson, C. L.; Rixey, W. G.; Garcia, A. A.; Frierman, M. "Use of Adsorbents for Recovery of Acetic Acid from Aqueous Solutions. I—Factors Governing Capacity". *Separ. & Purif. Methods* 1987, 16, 31–64.

Lipinsky, E. S.; Sinclair, R. G. "Is Lactic Acid a Commodity Chemical?". *Chem. Eng. Progr.* 1986, 82 (1), 26–32.

Lockwood, L. B. "Production of Organic Acids by Fermentation". In *Microbial Technology;* Peppler, H. J.; Perlman, D., Eds.; Academic: New York, 1979; pp. 356–387.

Mitchell, J. A.; Reid, E. E. "The Preparation of Aliphatic Amides". *J. Am. Chem. Soc.,* 1979, 53, 1879–1883.

Pearson, D. E.; Levine, M. "The Variation of Partition Ratios in Mixed Solvents". *J. Org. Chem.,* 1952, 17, 1356–1360.

Poole, L. J.; King, C. J. 1990. "Regeneration of Amine-Carboxylic Acid Extracts". Report No. LBL-28614; Lawrence Berkeley Laboratory: Berkeley, Calif., 1990.

Sato, M.; Nakahara, T.; Yamada, K. "Fermentative Production of Succinic Acid from n-Paraffin by *Candida brumptii* IFO 0731". *Agric. Biol. Chem.* 1972, 36, 1969–1974.

Starr, J. N., Dept. of Chemical Engineering, Univ. of California, Berkeley, personal communication, 1989.

Streitwieser, A., Jr.; Heathcock, C. H. *Introduction to Organic Chemistry;* Macmillan: New York, 1976; Chaps. 17 & 18.

Tamada, J. A.; Kertes, A. S.; King, C. J. "Extraction of Carboxylic Acids with Amine Extractants. I—Equilibria and Law-of-Mass-Action Modeling". *Ind. Eng. Chem. Res.* 1990, 29, 1319–1326 (1990).

Tamada, J. A. K.; King, C. J. "Extraction of Carboxylic Acids by Amine Extractants". Report No. LBL-25571; Lawrence Berkeley Laboratory: Berkeley, Calif., 1989.

Tamada, J. A.; King, C. J. "Extraction of Carboxylic Acids with Amine Extractants. III—Effect of Temperature, Water Co-extraction and Process Considerations". *Ind. Eng. Chem. Res.* 1990, 29, 1333–1338 (1990).

Urbas, B. "Recovery of Acetic Acid from a Fermentation Broth". U.S. Pat. No. 4,405,717. Sep. 20, 1983.

Urbas, B. "Recovery of Organic Acids from a Fermentation Broth". U.S. Pat. No. 4,444,881. Apr. 24, 1984.

Weast, R. C. *Handbook of Chemistry and Physics,* 54th ed., CRC: W. Palm Beach, Fla., 1974.

DISCLOSURE OF THE INVENTION

We have now found an improved process for isolating carboxylic acids from carboxylic acid-containing aqueous streams. Viewed as an overall process, the carboxylic acids are first removed from the aqueous stream by a sorption technique, such as a solid-phase adsorption or a liquid-phase extraction. In accord with this invention the sorbed carboxylic acid is then recovered by contacting the sorption phase with an aqueous solution of a low molecular weight alkylamine. This "back-extracts" the carboxylic acid into the aqueous extraction phase as an alkylammonium carboxylate. When this aqueous solution is heated and/or dewatered, the alkylammonium carboxylate decomposes to give rise to the carboxylic acid which can then be recovered. The alkylamine is also regenerated and can be recycled. Thus, a process is achieved which consumes no significant amount of chemicals and generates no significant amounts of waste by-product.

In one aspect, therefore, the present invention provides an overall process for recovering carboxylic acids from a carboxylic acid-containing aqueous feedstream. This process involves the following steps.

(a) The carboxylic acid-containing feedstream is first contacted with an acid-sorbing phase under conditions whereby the carboxylic acid is sorbed from the feedstream to the acid-sorbing phase. The acid-sorbing phase can be a solid or gel, ion-exchanger or other solid acid sorber, or it can be an acid-sorbing organic liquid extractant phase. This first step of the process forms an acid-depleted aqueous feedstream which can be discarded or further processed or recycled, as desired. It also provides an acid-enriched acid-sorbing phase.

(b) The acid-enriched acid-sorbing phase is then isolated.

(c) The isolated acid-enriched acid-sorbing phase is contacted with an aqueous solution of a water-soluble low molecular weight alkylamine. The alkylamine solubilizes the carboxylic acid from the sorbing phase into the aqueous solution as an alkylammonium carboxylate. This has the effect of regenerating the acid-sorbing phase so that it may be reused.

(d) The aqueous solution containing the low molecular weight alkylammonium carboxylate is then separated from the regenerated acid-sorbing phase.

(e) In the fifth step of this process, the aqueous solution of alkylammonium carboxylate is treated, under conditions such as by mild heating and dewatering, to decompose the alkylammonium carboxylate into the alkylamine and the carboxylic acid either as crystals or as a highly saturated solution, depending upon the tendency of the carboxylic acid to crystallize. The carboxylic acid can be simply recovered from this product. The alkylamine can also be taken off to drive the reaction in the direction of the desired decomposition and recovered, for example, as an overhead in distillation and recycled.

When the acid-sorbing phase is a liquid extractant, this process takes the form of a first liquid—liquid extraction from the aqueous feed in which the carboxylic acid is extracted with an acid-sorbent-containing organic phase. After separation of the two phases, the organic phase is back-extracted with an aqueous solution of low molecular weight alkyl amine. This gives a back-extract containing the carboxylic acid in the form of a low molecular weight alkylammonium carboxylate which can thereafter be dewatered and heated to free the alkylamine for recycle.

The acid-sorbing phase can also be a solid sorbent or a solid or gel ion exchange resin having base functionalities (amine or pyridyl, for example) which will react with and bind to the carboxylic acid to be recovered.

In another aspect, this invention provides a process for regenerating carboxylic acid-loaded solid or organic liquid-sorbing phases. This regeneration process involves contacting the acid-loaded solid or organic liquid acid-sorbing phase with an aqueous solution of low molecular weight alkylamine. In this way, the sorbed carboxylic acid is removed, and an aqueous solution of an alkylammonium carboxylate is formed. The alkylammonium carbonate is then isolated and decomposed to give the corresponding acid which is recovered and the corresponding amine which is recycled.

DETAILED DESCRIPTION OF THE INVENTION

BRIEF DESCRIPTION OF THE DRAWINGS

In this description of the invention, reference will be made to the accompanying drawings, in which.

DESCRIPTION OF PREFERRED EMBODIMENTS

Figure 1:
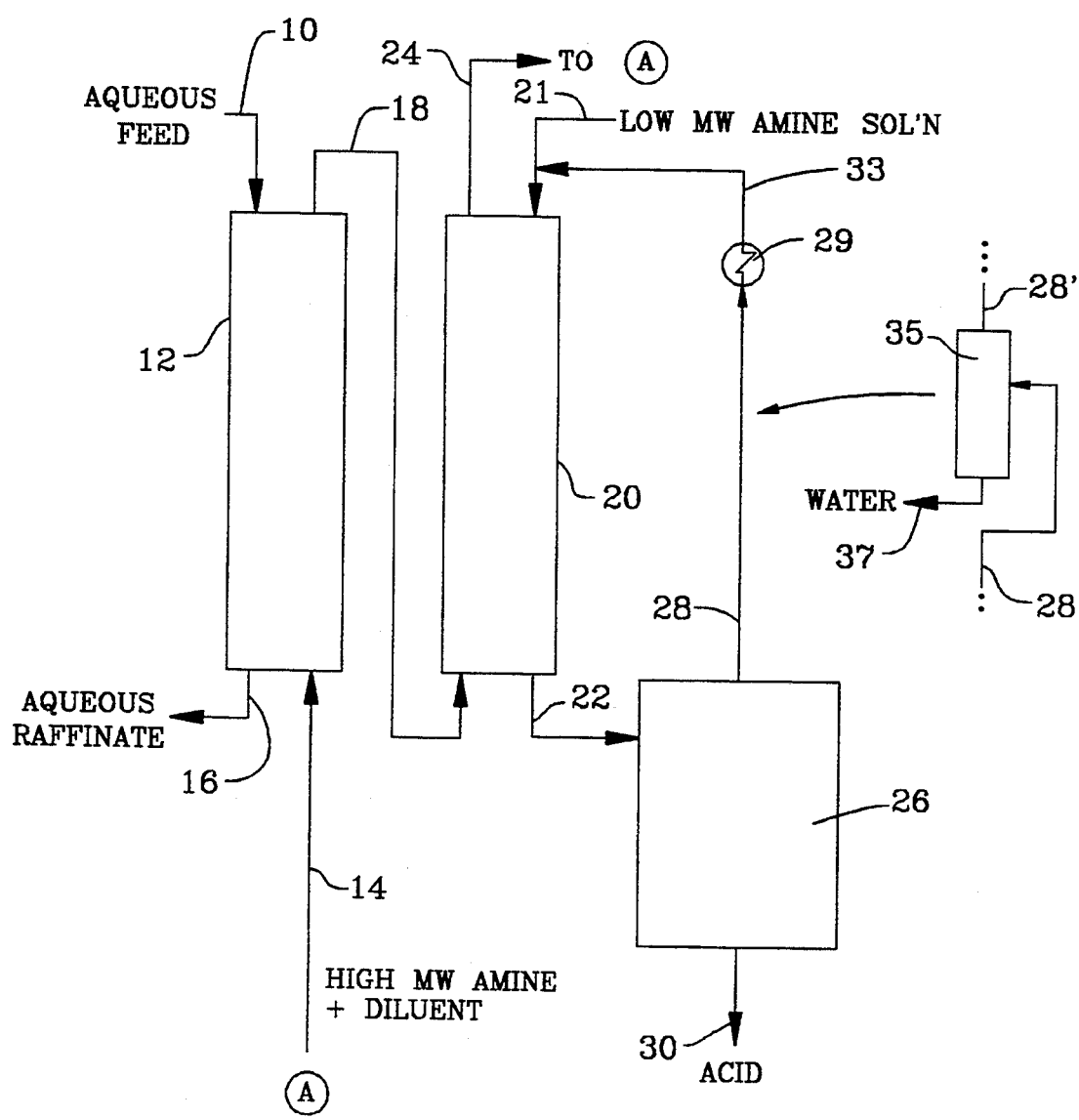
FIG. 1 is a schematic flow diagram illustrating the process of the invention embodied as a solvent extraction process.

This section is arranged as follows:

First, two representative embodiments of the process of the invention are described with reference to FIGS. 1 and 2.

Then, typical acids which may be recovered by the process are described.

Next, low molecular weight amines which may be used in the process are described.

Then, the various acid-sorbing organic phases, both liquid extraction and ion-exchange phases, will be discussed.

Finally, experimental details verifying the efficiency of the process will be given in the form of examples.

The Process

The present invention regenerates acid-loaded carboxylic acid-sorbing solids and organic liquid extractants by converting the sorbed carboxylic acids directly with water-soluble lower alkylamines to give aqueous solutions of lower alkylammonium carboxylates. These are then decomposed and optionally dewatered to yield the low molecular weight alkylamine and the carboxylic acid which is recovered. This regeneration process is illustrated as part of an overall solvent extraction process in FIG. 1. In FIG. 1 an aqueous feed stream which comprises a water-based solution having from a few parts per million to about saturation of carboxylic acid is fed through line 10 to countercurrent contactor 12. A liquid organic extractant is also charged to the contactor via line 14. In the case shown, the organic extractant has a density less than that of water so that the heavier aqueous feed moves down through an ascending stream of organic extractant. The organic extractant has acid-sorbing properties which enable it to preferentially pick up the carboxylic acid out of the aqueous feed. This acid-sorbing property can be inherent in the organic liquid such as a ketone (for example, methyl isobutyl ketone (MiBK)) or, alternatively, the liquid organic phase can contain a carboxylic acid-sorbing material (for example, an organic amine extractant). A typical acid-sorber is an alkyl amine having a straight chain alkyl long enough to impart significant solubility in the organic phase, for example, tri-n-octylamine.

The contacting of the aqueous feed with the acid-sorbing organic liquid extracts the carboxylic acid from the aqueous feed, giving rise to a acid-lean aqueous raffinate which is removed via line 16. The carboxylic acid-rich extract is removed via line 18 to a second counter-current contactor 20. In contactor 20 the acid-rich organic stream is passed upward through a descending stream of low molecular weight alkylamine which is dissolved in water provided by line 21. The low molecular weight alkylamine reacts with the acid present in the organic phase to give rise to a low molecular weight alkylammonium carboxylate. This carboxylate is soluble in the water phase and is removed from contactor 20 as the aqueous extract via line 22. The organic raffinate generated by this second extraction includes the organic solvent as well as the optional acid-sorbing material. This raffinate is removed from contactor 20 via line 24 and may be recycled advantageously to line 14 and reused. The alkylammonium carboxylate-containing aqueous stream removed via line 22 is passed to dewatering/decomposing zone 26. There, heat and/or reduced pressure are applied so as to remove water and decompose the alkylammonium carboxylate into the corresponding low molecular weight alkylamine and carboxylic acid. If, as is usually the case, the alkylamine is more volatile than the acid, the alkylamine can be taken off along with water. The mixture of water and low molecular weight alkylamine can be taken overhead via line 28 condensed in condensor 29 and recycled to line 21 via line 33. This overhead mixture can be fractionated, if desired or necessary, to a water stream removed via line 37 and an alkylamine stream (line 28') by fractionation column 35 or the like. The alkylamine, with whatever accompanying amount of water is present, is condensed in condensor 27 and is then recycled through line 33 to column 20 as shown. The acid which is freed by this decomposition and amine removal is removed via line 30.

Figure 2:
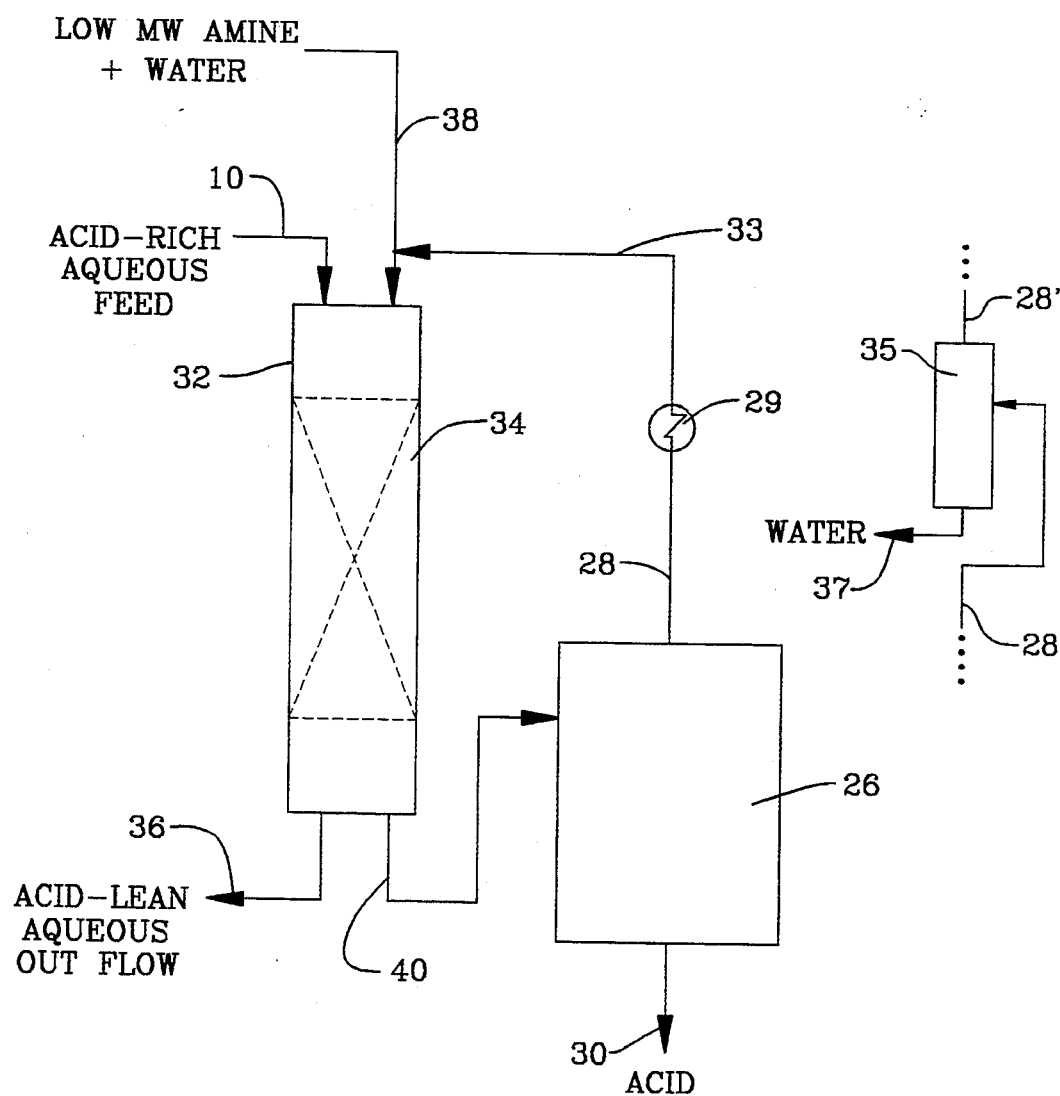
FIG. 2 is a schematic flow diagram of the process of this invention embodied as an ion-exchange process.

The apparatus described with reference to FIG. 1 is merely representative. In place of the countercurrent contactor 12 or countercurrent contactor 20, one can, for example, use a mixed vessel and a settling zone (phase separation zone), or a cocurrent extractor. The countercurrent contactor itself can be baffled, and can have rotating discs or the like as desired. Similarly, the dewatering/decomposing zone 26 can operate at elevated temperatures, for example up to 150° C. and preferably from 30° C. up to 140° C. Also advantageously, zone 26 can be evacuated such as to absolute pressures of 0.75 atmospheres or below, especially 0.5 atmospheres or lower such as to 0.01 atmospheres. A moving dry gas phase, especially an oxygen-free gas phase, can also be present to assist the dewatering-decomposition. It is additionally possible to enhance the efficiency of these extraction-back extraction steps by applying temperature gradients between the two extraction zones, i.e., if this will assist in extracting acid from the aqueous feed or back-extracting acid into the lower alkylamine/-water back-extractant.

Although the exact conditions employed will depend in part on the equipment employed and in part upon the volume and exact nature of the feedstock and extractants, the residence time for the feedstock in the first extractor typically ranges from about one minute to about two hours and more typically from about five minutes to about one hour. Also typically the volume ratio of aqueous feed to organic extractant fed to contactor 12 will range from about 30:1 to about 1:3, depending, in part, upon the concentration of acid.

It is generally preferred to use a volume of organic extractant and a concentration of optional acid-sorbing material adequate to remove a substantial fraction of the desired carboxylic acid from the aqueous feed. This generally means that the number of equivalents of acid-sorbing groups such as amines or the like present in the liquid extractant or its optional dissolved acid-sorbing material should exceed or at least equal the number of equivalents of acid present in the aqueous feed.

In the back-extraction stage, again, residence times are typically selected from about one minute to about three hours, although longer times may be used if convenient. Also, it is desirable to use a relatively concentrated solution of low molecular weight alkylamine in the back-extraction. For this purpose, the alkylamine may be dissolved under pressure, if desired. It does appear, however, that substantially complete back-extraction occurs whenever the amount of lower alkylamine in equivalents in the aqueous back extractant is approximately equal to or greater than the number of equivalents of carboxylic acid being recovered from the organic phase. Typically, very complete back-extraction occurs with from about 1.0 to 1.5 equivalents of amine based on acid. Although larger amounts of the lower alkylamine can be used, it appears that essentially complete recovery of the carboxylic acid is achieved at about this number of molar equivalents. Of course, excesses of low molecular weight alkylamine can be used if desired and, if only partial recovery of the carboxylic acid is desired, lower amounts of alkylamine material may be used, accordingly.

In the dewatering/decomposition stage 26, the exact amount of water removed can vary up to essentially complete removal of water, i.e., to residual water levels of from as low as 1% to say 75%. This stage primarily serves to decompose the carboxylate into the free alkylamine and the free acid. As the decomposition progresses, either the free acid or the free amine is removed, driving the decomposition forward and permitting a more complete decomposition of the carboxylate and recovery of acid. In the embodiment shown in FIG. 1, the amine is taken overhead and removed, and the acid is removed as well.

The dewatering/decomposition step is carried out under relatively mild conditions such as a temperature of from about 20° C. to about 200° C. and particularly 30° to 175° C., an average residence time of from about 1 minute to 3 hours and especially 2 minutes to 2 hours, and a pressure from about 50 torr (vacuum) to about 2 atmospheres.

In determining how much water to remove, the extent to which the salt is decomposed, and the conditions used to effect these processes, one must bear in mind the fact that the free carboxylic acids can react with non-tertiary alkyl amines (i.e., monoalkylamines or dialkylamines) to give amides. If a non-tertiary-alkyl amine is present and is exposed to the carboxylic acid for prolonged periods at elevated temperature, a lower yield may result.

Ultimately, the acid should be obtained as free of residual alkylamine carboxylate and contaminating alkylamine as possible. This can be facilitated by various washings, crystallizings and the like as needed. Representative levels of carboxylate decomposition range from about 25% up to essentially 100%.

The process of this invention not only works in a solvent extraction setting as described with reference to FIG. 1, but also can be employed in an ion exchange process or other solid phase sorption process. Such a process is shown representatively in FIG. 2. In FIG. 2, again, an acid-rich aqueous feed is charged through line 10, this time to an ion exchange unit or solid/gel sorption unit 32. Unit 32 contains a bed of solid sorbent, for example, ion exchange material 34. This solid or gel sorbent may be a relatively basic material such as an amine-containing resin or the like so as to adsorb selectively the carboxylic acid groups out of the acid-rich aqueous feed. The sorbent thus gives rise to an acid-lean aqueous outflow which is taken out of contactor 32 via line 36. The outflow in line 36 can be suitably monitored until a breakthrough in carboxylic acid level is noted in the outflow, indicating that the solid sorbent 34 has removed its capacity of carboxylic acid. At this point, feedline 10 is closed via means not shown and aqueous outflow line 36 is also closed. An aqueous solution of low molecular weight alkylamine is then fed to contactor 32 via line 38. The low molecular weight alkylamine and the solid sorbing phase are matched so that the low molecular weight amine is a stronger base than the ion exchange solid or other noted sorber. This causes the low molecular weight trialkylamine to react with the sorbed carboxylic acid and form an alkylammonium carboxylate, which is soluble in water and thus carried out of contactor 32 via line 40. This stream is then passed to dewatering/decomposing zone 26. As described with reference to FIG. 1, the stream is dewatered and decomposed so as to give rise to a vaporized stream made up of water and alkylamine. This overhead is taken off via line 28 to condensor 29. The condensate from 29 is recycled via line 33 to column 32. Optionally the overhead from zone 26 is passed via line 28 to fractionation column 35. There it is split to isolate some or all of its water content which is removed via line 37. The amine content of the overhead is passed via line 28' to condensor 29 and recycled via line 33. Zone 26 produces a bottom product made up of the recovered carboxylic acid which is removed via line 30.

In the process shown in FIG. 2, the amount of lower alkylamine should be selected along the same lines described with reference to FIG. 1. That is, if complete recovery of carboxylic acid is desired, at least about one equivalent of low molecular weight alkylamine should be used for each equivalent of acid being recovered. If a lower degree of recovery can be tolerated or is desired, lower amounts of alkylamine may also be used.

It is generally preferred to carry out the steps of this process, especially the decomposition/dewatering, in an oxygen-free or reduced-oxygen environment such as an inert gas blanket to minimize decomposition of the amine itself.

The acid recovered via line 30 in either of these processes is typically present as a slurry of solid in aqueous liquid or as a saturated/supersaturated solution of acid. This stream can be further processed to further dewater the acid-containing material, to decolorize it, further remove amine from it and otherwise purify it. These steps are optional.

This process can be practiced in a batch mode, as well, if desired.

The Acids Recovered

The acids liberated and recovered in the regeneration process of the invention are carboxylic acids. These acids include aliphatic carboxylic acids of 2-16 carbons and aromatic carboxylic acids of 7-20 carbons. The aliphatic carboxylic acids include 2-16 carbon monoacids such as acetic acid, propionic acid, butyric acid, pentanoic acid, hexanoic acid, octanoic acid, dodecanoic acid and the like. The process is especially effective with polycarboxylic acids such as the di-, tri- and higher carboxyl materials, including the commonly known even-carbon-numbered diacids of 2-12 carbons (that is, the better known dicarboxylic acids of 2, 4, 6, 8, 10 or 12 carbon atoms, such as oxalic acid, succinic acid, sebacic acid, adipic acid and fumaric acid). Of course, the process also works with the odd-numbered acids, as well. Lactic acid, malic acid and citric acid are representative hydroxy-containing acids which can be recovered by this process.

The aromatic acids include aromatic monoacids of 7-13 carbons such as benzoic acid, cinnamic acid, phenylacetic acid, naphthoic acid, and the like, and diacids of 8-12 carbons such as phthalic acid. In addition to the simple oxyhydrocarbon acids, the process can be used to recover those more complex materials such as amino acids, and the like, which are of value and which often occur in aqueous solutions and need to be recovered therefrom.

Functional groups such as halogens or nitro groups may be present in the carboxylic acids recovered by the process of this invention.

When these acids are initially present in and recovered from water-based feedstocks in an overall sorption-regeneration process, the feedstocks will contain from about ten parts per million to saturation (for example, up to about 40% by weight) and especially from 0.1% to 25% by weight of recoverable carboxylic acids. The feedstocks can contain a mixture of these acids, in which case the present process can either recover all of the acids or, if differences in forward sorption or back-extractability with the alkylamine permit, can fractionate the acid mixture. The present invention finds application with prepared feedstocks such as fermentation broths and the like; it also finds application with contaminated aqueous streams. Accordingly, the feedstocks can contain other materials such as salts and organics (sugars, starches, alcohols, aldehydes and the like). Typically, however, these other materials do not substantially follow the carboxylic acids as they are sorbed and back-extracted. Thus, they do not significantly interfere with the process of this invention.

As noted, these acid materials removed and recovered by the process range in size from about 2 carbons (acetic acid) to about 16 carbons and can include monocarboxylic acids, di-and polycarboxylic acids, hydroxycarboxylic acids, and the like. The acid can be aliphatic or aromatic. This wide range of materials spans a range of physical forms: A few of these acids, for example, the 2 to 4 carbon monocarboxylic acids, are relatively volatile liquids.

| | |
|---|---|
| $C_2$ - Acetic Acid | 118° C. b.p. |
| $C_3$ - Propionic Acid | 141° C. b.p. |
| $C_4$ - Butyric Acid | 165° C. b.p. |

Lactic acid is hard to crystallize and usually exists as a concentrated viscous solution. Many of the rest of these acids, especially the dicarboxylic acids, exist as insoluble solids at room temperature. The physical form of the free acids can play a part in the selection of the low molecular weight alkylamine employed in the regeneration.

As noted previously, in the carboxylate decomposition/dewatering steps of the regeneration process, a forward driving force is needed to assure substantial conversion of the carboxylate. This driving force typically is provided by separating the free amine from the free acid and removing one or both products from the reaction zone. Preferential vaporization of one product from the other is very convenient and preferred way to carry out this separation.

The Low Molecular Weight Alkylamine

A key element of the present invention is the use of an aqueous solution lower alkylamine as the back-extractant (desorbant) material. This alkylamine material is also sometimes referred to herein as a low molecular weight amine or the like.

The lower alkylamine can be a mono-, di- or trialkylamine. It is selected so that solubility in an aqueous phase is favored. In the extraction/back-extraction embodiment, the lower alkylamine should be selected so as to have a partition coefficient $$\frac{[\text{Concentration in Aqueous Phase}]}{[\text{Concentration in Organic Phase}]}$$

of at least 1, preferably at least 2 and more preferably at least 3. It is also advantageous if the lower alkyl amine has a solubility in the aqueous back-extraction solvent (which is water or water with up to about 10% by volume of lower (1 to 3 carbon) alkanol), of at least about 1% by weight and preferably at least about 2% by weight.

Of these materials, the trialkylamines offer an advantage of not being capable of forming amides with the recovered acids. The mono- and dialkyl materials can enter into this irreversible side reaction if prolonged contact with the acid at elevated temperatures occurs.

Another factor to be taken into account in selecting an amine is its boiling point relative to the boiling point of the aqueous back-extraction solvent and the free acid. If volatilization of the amine is to be used as the mechanism to separate the amine from the acid, a difference in boiling point between them is necessary.

Still another factor to be taken into account in selection of an amine is the susceptibility of the amine to thermal decomposition and/or oxidation.

Of the trialkylamines materials, preference is given to trimethylamine for a number of reasons. First, it is the most common and least expensive of these materials. Also, it has a high solubility in water and thus allows a concentrated back-extract to be formed. Third, it is the most volatile of the trialkylamines (2.9° C. b.p.) and thus, upon decomposition of the trimethylammonium carboxylates, can be removed overhead by distillation with the least amount of heating of the decomposing carboxylate and resulting acid. Other trialkylamines containing up to about 6 or even 8 total carbon atoms—for example dimethylethylamine, methyldiethylamine, triethylamine, dimethyl-n-propylamine, dimethyl-i-propylamine, methyldi-n-propylamine, dimethylbutylamine and the like—may be used. Monoalkylamines of up to about 6 carbons such as methylamine, ethylamine, propylamine, butylamine, pentylamine and hexylamine and dialkylamines of up to about 8 total carbons such as dimethylamine, diethylamine, dibutylamine and the like can also be used as long as their potential for side reactions is kept in mind. Mixtures of amines can be used.

In the process of this invention, these alkylamines are employed as an aqueous solution (optionally containing up to 10% alkanol). This solution is generally made as concentrated in amine as possible. It can, however, range in concentration from about 1% to saturation, which is about 25%–50% by weight in the case of the more soluble of these amines, such as trimethylamine. The aqueous solution of alkylamine can contain other materials added to improve or facilitate processing. These can include antifoam agents, corrosion inhibitors, and the like, as will be known to those of skill in the art. The amine concentration can be increased by dissolving under pressure of up to about 5 atmospheres as well.

The Organic Phase

When this regeneration process is used in a liquid—liquid extraction context, the organic phase from which the acids are back extracted is an organic liquid of limited water miscibility. The term "limited water miscibility" is defined to mean that the organic liquid must be capable of forming a second phase when mixed with water and having a maximum water uptake of not more than about 20% by weight of water. This water uptake is based on a two component organic solvent-water system.

The organic phase liquid can be a single material or it can be a mixture of materials. Ketones having 4 to 8 carbons, for example methyl isobutyl ketone, methyl n-butyl ketone, methyl pentyl ketone, diethyl ketone and the like, can be used as extracting solvents. Cyclic ketones have given very good results. These contain from 5 to about 10 carbons with 5 or 6 carbons making up a 5- or 6-membered aliphatic ring and the remainder being alkyl substituents off the ring. Cyclopentanone, cyclohexanone, methyl cyclohexanone, dimethyl cyclohexanone, and diethyl cyclohexanone are examples of suitable organic phase liquids for use herein. Six to 10 carbon alcohols such as n-hexanol, cyclohexanol, heptanol, n-octanol, 2-ethyl hexanol, nonanol, and the like can be used. Four-to 8-carbon ethers such as diethyl ether, methyl butyl ether, methyl pentyl ether, and ethyl butyl ether can also be used. Five to 8 carbon esters such as butyl acetate, pentyl acetate, and the like can be used as well.

The Acid Sorber

The organic liquid phase can also contain up to 80% by weight of an amine or other basic acid sorber to enhance the uptake of acid. This material is optional. Typical amines known to be useful in solvent extraction systems include trialkyl amines having at least one 6–12 carbon alkyl group and in total from about 20 to about 36 carbons in their three alkyl groups. Such materials include trioctyl/decyl amine, e.g., Alamine 336, (Henkel Corp.), Adogen 363 (Rohm & Haas Corp.) and similar amines marketed by Hoechst. These materials are characterized as being much less soluble in water than the low molecular weight alkylamines which are used to back-extract the acid from the organic phase.

Preferred organic phases are cyclohexanone, methyl cyclohexanone, methyl isobutyl ketone, and methyl n-butyl ketone, alone or together with up to about 80% by weight of an amine.

Solid Sorbent Materials

In an alternative embodiment, the aqueous solution of lower alkylamine is used to resolubilize carboxylic acid adsorbed onto a solid or gel adsorbent. These solid phase materials include high surface activity relatively inert materials such as carbon black, or the like. Representative carbon black adsorbents are listed in Table 1.

TABLE 1

| Activated Carbon Solid Adsorbents | |
|---|---|
| Carbon | Source |
| Witcarb 950 | Witco |
| Columbia | Witco |
| G-BAC | Union Carbide |
| GX-031 | Amoco |
| Row 0.8S | Norit |
| Filtrasorb | |
| 100 | Calgon |
| 200 | Calgon |
| 300 | Calgon |
| 400 | Calgon |

TABLE 1-continued

Activated Carbon Solid Adsorbents

| Carbon | Source |
| --- | --- |
| 100 OX | Calgon |
| XE-340 | Rohm & Haas |
| SE-348 | Rohm & Haas |

They also include basic ion exchange resins such as pyridyl, pyridinium, amine and ammonium group-containing resins. While defined as "ion exchange" resins it will be appreciated that in many cases these materials are used for their basicity (amine functionality) and not for their ionic exchange potential. These materials include resins with these groups as part of their backbone structure as well as materials which have these groups appended from their backbones. These resin materials are available commercially as basic ion exchange resins. Representative resins are listed in Table 2.

TABLE 2

Ion Exchange Solid Adsorbents

| Commercial Designation | Source | Type of Adsorbent |
| --- | --- | --- |
| AMBERLITE | | |
| XAD-2 | Rohm & Haas Corp. | Styrene-Divinylbenzene Copolymer |
| XAD-4 | Rohm & Haas Corp. | Styrene-Divinylbenzene Copolymer |
| XAD-7 | Rohm & Haas Corp. | Acrylic ester-Divinylbenzene Copolymer |
| XAD-12 | Rohm & Haas Corp. | Poly (N oxide) |
| XE-309 | Rohm & Haas Corp. | Poly(4-Vinylpyridine) |
| XE-378 | Rohm & Haas Corp. | Poly(2-Vinylpyridine) |
| AMBERSORB | | |
| XE-340 | Rohm & Haas Corp. | Pyrolyzed Sulfonated Styrene-Divinylbenzene Copolymer |
| XE-348 | Rohm & Haas Corp. | Pyrolyzed Sulfonated Styrene-Divinylbenzene Copolymer |
| DOWEX | | |
| WGR | Dow Chemical Company | Epoxy Polymer with Tertiary Amine Groups |
| MWA-1 | Dow Chemical Company | Styrene-Divinylbenzene Copolymer with Tertiary-Amine Groups |
| A-340 | Diamond Shamrock, Inc. | (Duolite) Polyethylene-Diamine, Cross-linked with Epichlorohydrin (a gel-type resin) |
| AG3-X4 | Bio-Rad | Epoxy-amine Polymer with Primarily Tertiary Amine Groups and ~100% Quaternary Groups |
| Reillex | | |
| 425 | Reilly Tar & Chemical Co. | Poly(4-Vinylpyridine) |
| 402 | | |

Experimental

This invention will be further illustrated by the following Examples.

These examples set forth a series of experiments which confirm each of the steps of the present process with three representative carboxylic acids, lactic acid, succinic acid, and fumaric acid.

EXAMPLES 1-3

Reagents

The reagents used and their sources are given in Table 3.

TABLE 3

Sources and Description of Chemicals Used

| Compound | Supplier | Description |
| --- | --- | --- |
| Alamine 336 | Henkel Corp. | 3° amine, $C_8$–$C_{10}$ straight chain |
| Fumaric acid (crystalline) | Aldrich, Inc. | 99% purity |
| Lactic acid | Mallinckrodt, Inc. | 85 wt % aqueous solution |
| Methyl isobutyl ketone (MiBK) | Aldrich, Inc. | 99.7% purity |
| Succinic acid (granular) | Mallinckrodt, Inc. | analytical grade |
| Trimethylamine (TMA) | Aldrich, Inc. | 25 wt % aqueous solution, (manufactured by adding 99% anhydrous TMA to water) |

Distilled water that had been passed through a Milli-Q purification system (Millipore Corp.) was used when necessary.

Equipment

High performance liquid chromatography (HPLC) analysis was carried out using a Spectra-Physics SP 8000B chromatograph and a differential refractometer detector (Waters Model No. R401). Either a $C_{18}$ Radial-Pak Resolve column (Waters Associates) contained in a radial compression module (Waters, RCM-100) or an organic acid column (Biorad AMINEX Ion Exclusion HPX-87H) was used. The mobile phase was 0.01N $H_2SO_4$.

Gas chromatography (GC) analysis was carried out using a Varian Model 3700 chromatograph with a flame ionization detector and a Hewlett-Packard 3390A integrator. Samples (1 μl) were injected into a 3.2 mm × 152 cm stainless steel column packed with 5% silicone OV-17 on acid-washed, DMCS-treated, 80/100 mesh Chromosorb W (Alltech Associates). The injector temperature was 290° C. The column temperature was held at 35° C. for 2 minutes and then increased to 240° C. at a rate of 10 C./min. Nitrogen was used as the carrier gas.

Aqueous-phase pH values were determined using an Orion 701A pH meter equipped with an Orion semimicro Ross ™ pH electrode. Flasks containing two-phase extraction systems were placed in a shaker bath—either a Fisher Scientific Versa-Bath S or a Lab-Line Orbit Water Bath Shaker.

Alamine 336 Extracts of Carboxylic Acids

Equal volumes of an aqueous solution of the acid were contacted with a solution of 0.3M Alamine 336 in MiBK to extract the acid into the organic phase. For lactic acid, the two phases were contacted in a separatory funnel and then transferred to erlenmeyer flasks which were placed in a 25° C. shaker bath, for two days to allow the phases to settle. Vigorous shaking in a separatory funnel of an aqueous solution of succinic acid with the organic amine solution was found to result in emulsion formation; therefore, for both succinic acid and fumaric acid, the two phases were placed directly in erlenmeyer flasks. The flasks were put in a 25° C. shaker bath for two to three days. In the case of fumaric acid, solid crystals were added with the initially saturated aqueous phase, in order to obtain sufficiently high final concentrations of fumaric acid.

After the contacting, each phase was removed by pipet. The pH of the aqueous phase was measured. The amount of acid remaining in the aqueous phase was determined by titration with aqueous NaOH. The concentration of acid in the organic phase was determined by two-phase titration with aqueous NaOH.

Back-Extraction Experiments

Back-extractions into aqueous trimethylamine (TMA) were carried out at 25° C. in a separatory funnel with an organic to aqueous phase ratio of 8/3 (v/v). The two phases were then transferred to erlenmeyer flasks. The flasks were placed at 25° C. in a shaker bath for two days to allow the phases to settle. The phases were separated by pipet.

GC analysis of the organic phase was used to determine the extent to which TMA had been transferred to the organic phase. For the aqueous phase, the concentration of acid was determined by HPLC analysis using the $C_{18}$ column.

The concentration of acid remaining in the organic phase was determined by HPLC analysis of an aqueous NaOH extract of the organic phase, using the $C_{18}$ column. The NaOH extract was obtained by contacting a 5 ml sample of the organic phase with an excess of aqueous NaOH in a centrifuge tube. The two phases were mixed with a magnetic stir bar and then centrifuged for 30 minutes at 2000 rpm to separate the phases.

Thermal Decomposition Experiments

Figure 3:
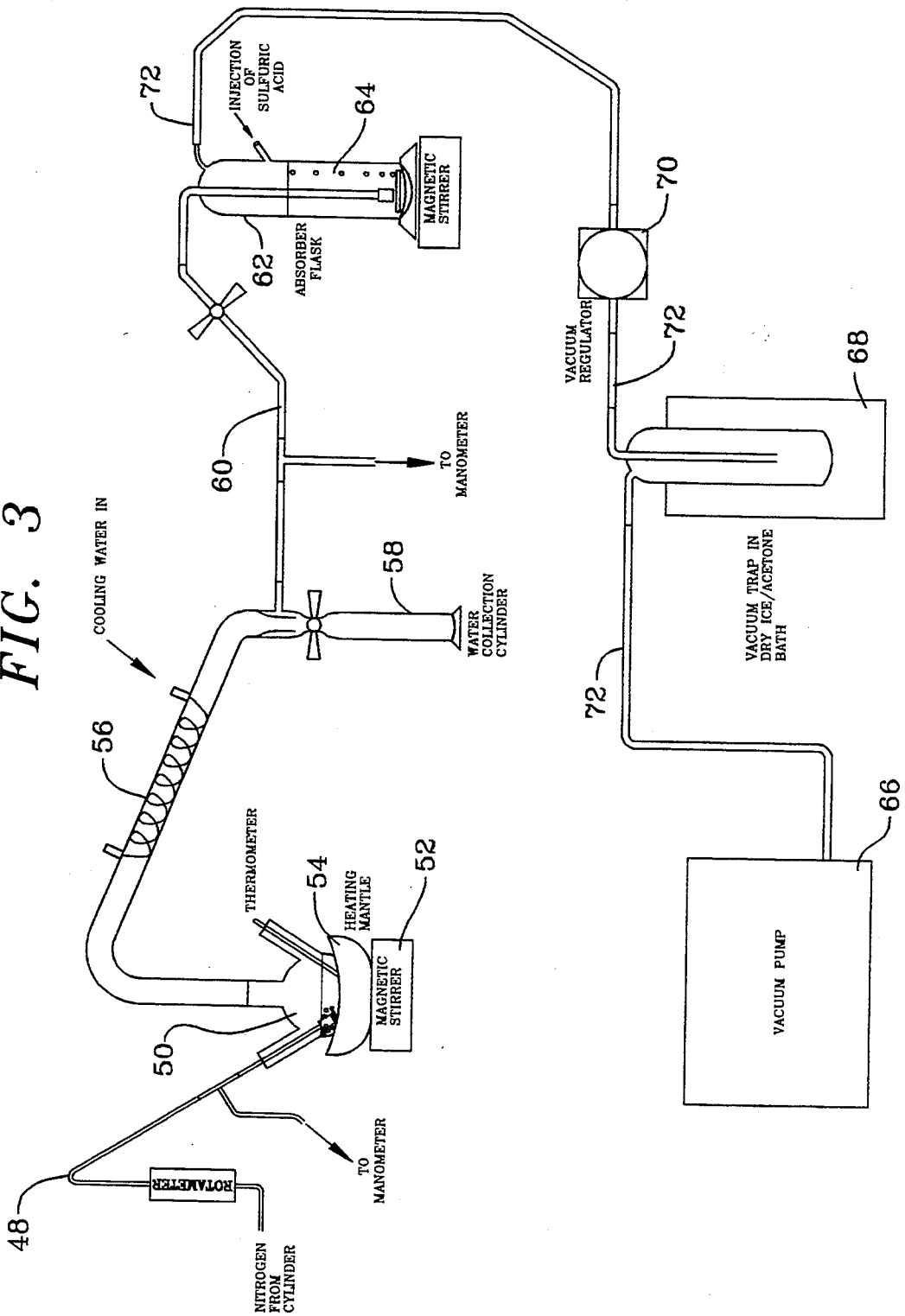
FIG. 3 is a schematic representation of an apparatus used in experiments to verify aspects of the process of this invention.

Aqueous solutions of trimethylammonium carboxylates were heated under nitrogen to prevent possible oxidation of the TMA. The apparatus used in these experiments is shown in FIG. 3.

The aqueous solution (60 ml) was placed in a three-neck 100-ml round-bottom flask 50 operated under vacuum and equipped with a magnetic stir bar 52 and a heating mantle 54. Water driven off from the solution was condensed in condensor 56 and collected in a graduated cylinder 58. Most of the TMA evolved was carried through line 60 collected in an absorber flask 62 containing dilute $H_2SO_4$ 63.

Nitrogen was bubbled through the aqueous trimethylammonium carboxylate solution via line 48. A vacuum (to 350-380 mm Hg absolute) was pulled on the reaction train via vacuum regulator 70, trap 68 and pump 66, all on line 72.

The temperature of the aqueous trimethylammonium carboxylate solution was allowed to increase gradually, reflecting the increase in boiling temperature of the solution, until a point was reached when most of the water had been removed. At this point, a sharp increase in temperature was observed. Heating was adjusted to keep the temperature below 130° C.

At the end of the run, a sample of the water collected was titrated with 0.03N $H_2SO_4$ in order to determine the TMA content. For total pressure in the range 350 to 380 mg Hg, less than 2% of the total TMA was present in the water. A sample of the final absorber solution was titrated with 0.01N or 0.1N NaOH.

The moles of TMA and the volume of water collected versus time and the nitrogen flow rate were used to determine the partial pressures of water vapor and TMA as functions of both temperature and the concentrations of salt and free acid in solution.

After the trimethylammonium carboxylate salt was concentrated and thermally decomposed as described above, there remained behind a light yellow mixture of carboxylic acid and residual water and TMA (probably in the form of the trimethylammonium carboxylate). In the cases of fumaric and succinic acids, crystals of the acid were present. These acids were removed and purified.

Back-extraction into Aqueous TMA

During the back-extraction experiments, the concentration of acid in the extract was held constant while the TMA concentration was varied. Results for the three different acids are shown as data points in FIGS. 4, 5 and 6. For all three acids, essentially 100% of the acid was back-extracted into the aqueous phase at conditions in which there was at least one mole of TMA for every equivalent weight of acid. This is a sign that the basicity of aqueous TMA ($pK_b=4.1$) is much stronger than that of the organic amine, as would be expected.

Figure 4:
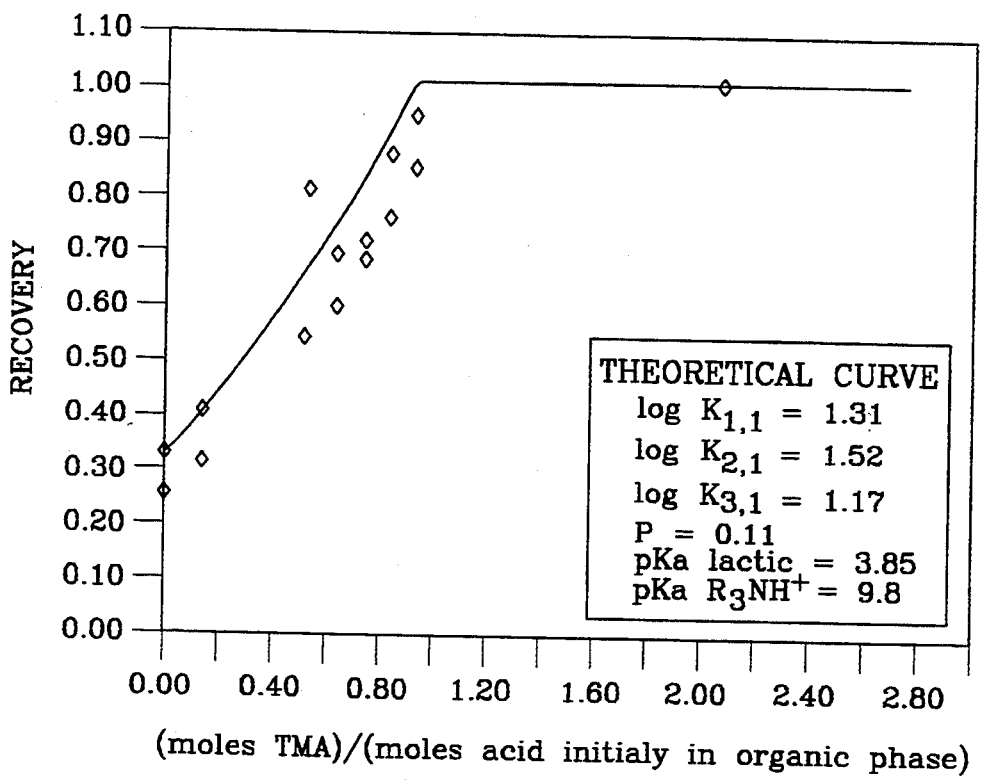
FIG. 4 is a graph illustrating the recovery possible using the process of this invention to back-extract lactic acid from an organic extract using trimethylamine as a low molecular weight amine.
Figure 5:
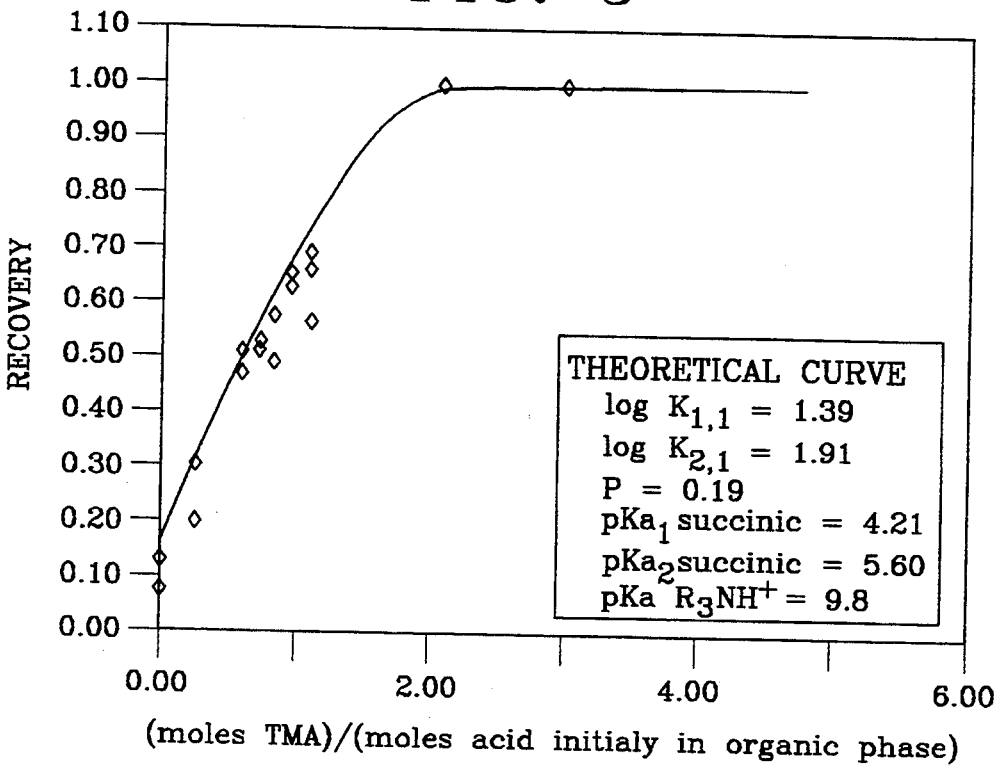
FIG. 5 is a graph illustrating the recovery possible using the process of this invention to back-extract succinic acid from an organic extract using trimethylamine as a low molecular weight amine.
Figure 6:
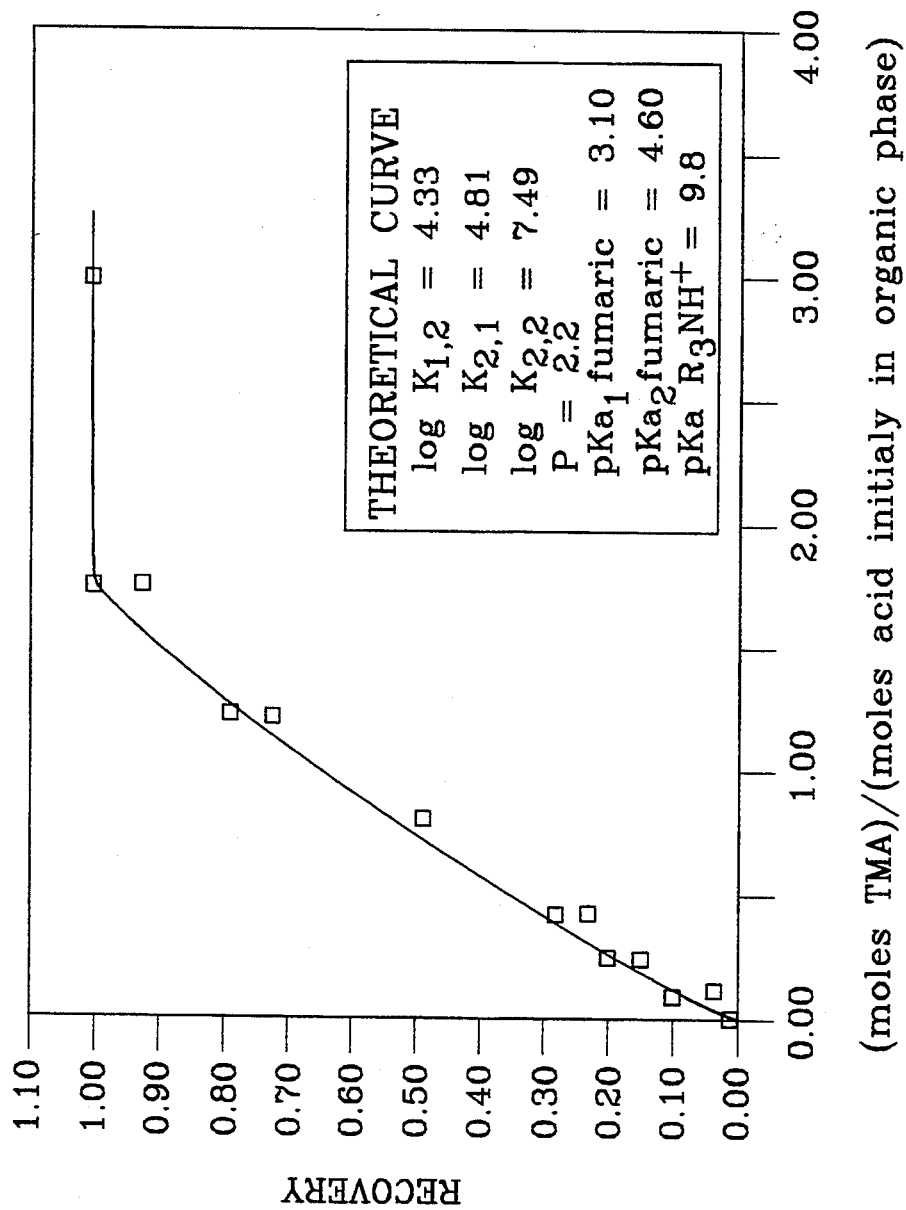
FIG. 6 is a graph illustrating the recovery possible using the process of this invention to back-extract fumaric acid from an organic extract using trimethylamine as a low molecular weight amine.

The curves shown in FIGS. 4 through 6 result from a complexation model, which includes chemical-equilibrium and mass-balance equations that describe the system. There are no fitted parameters. In all three cases, the back-extraction equilibrium data compare well with the predictions of the model.

The solubility of the acid in the amine-free diluent can be accounted for by use of the partition coefficient, P, defined as the concentration of uncomplexed acid in the organic phase divided by the concentration of unionized acid in the aqueous phase. The partition coefficients between MiBK and water, concentration basis, at 25° C. are 0.11, 0.19, and 2.2 for lactic, succinic and fumaric acids, respectively (Tamada and King, 1989; Starr, 1989).

In the back-extraction experiments, the equilibrium concentration of TMA in the organic phase was less than 0.0005 wt. %, as long as the overall molar ratio of TMA to acid was less than or equal to that corresponding to stoichiometric equivalence. This presumably reflects full ionization and pairing of the TMA with the acid in the aqueous phase.

When TMA was present in excess of the stoichiometric ratio, partitioning of TMA into the organic phase was substantially greater. Representative organic-phase concentrations of TMA were 2.5, 1.4 and 0.55 wt. % for 2.1 moles TMA/mole lactic acid, 3.1 moles TMA/mole succinic acid, and 3.0 moles TMA/mole fumaric acid, respectively. Pearson and Levine (1952) report the partition coefficient of uncomplexed TMA into MiBK from water (wt. fraction basis) to be 1.88.

Thermal Decomposition of Carboxylates

Lactic Acid

As an aqueous solution of lactic acid is concentrated by heating, crystalline lactic acid does not precipitate. Instead, the viscosity of the solution increases steadily as self association of the acid occurs.

In the thermal regeneration experiments carried out with aqueous solutions of trimethylammonium lactate, the goal was therefore to remove essentially all the TMA, leaving behind a concentrated aqueous solution of lactic acid and lactic acid polyesters, similar to the commercial syrup. When 45 mL of 1.6N lactic acid and 1.89N TMA in water was heated at 101°-120° C. and 300 mm Hg for 28 hours, only 63% of the water and 62% of the TMA present in the initial aqueous solution were removed, leaving behind a viscous aqueous solution. The increasing ratio of lactic acid to TMA, without precipitation of the highly soluble acid, would serve to depress the volatility of the residual TMA. Also, formation of intermolecular esters in concentrated solutions may impose severe transport limitations, hampering further TMA removal.

Succinic Acid and Fumaric Acid

Figure 7:
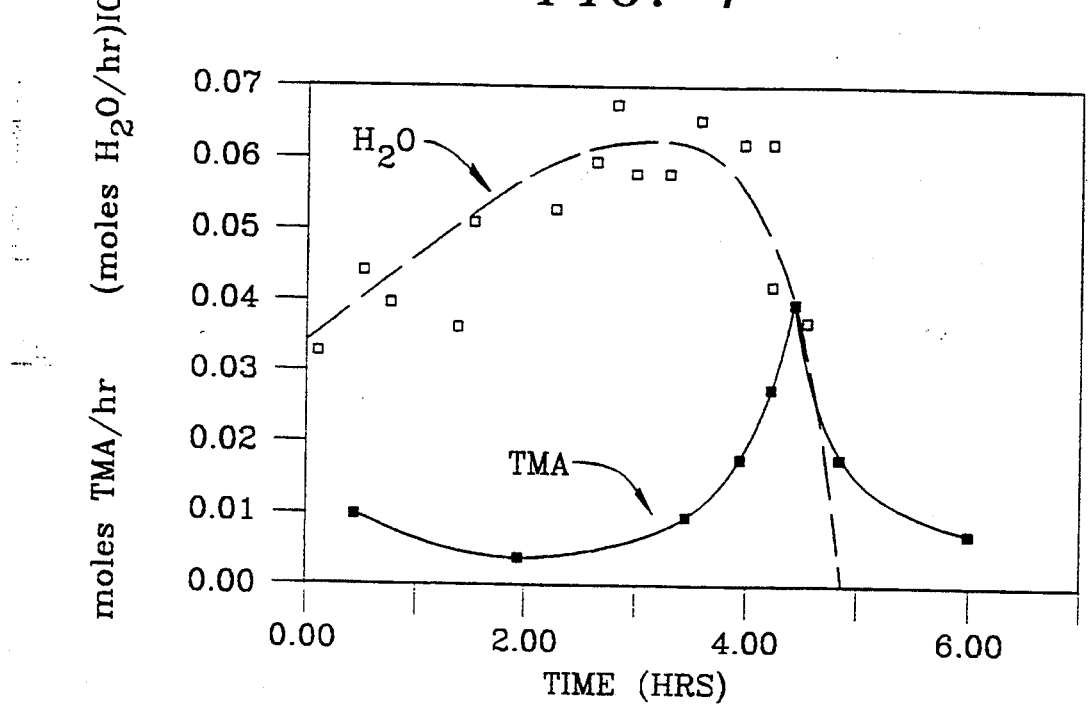
FIG. 7 is a graph showing rates of removal of water and trimethylamine during dewatering/decomposition of a trimethylammonium succinate salt solution.
Figure 8:
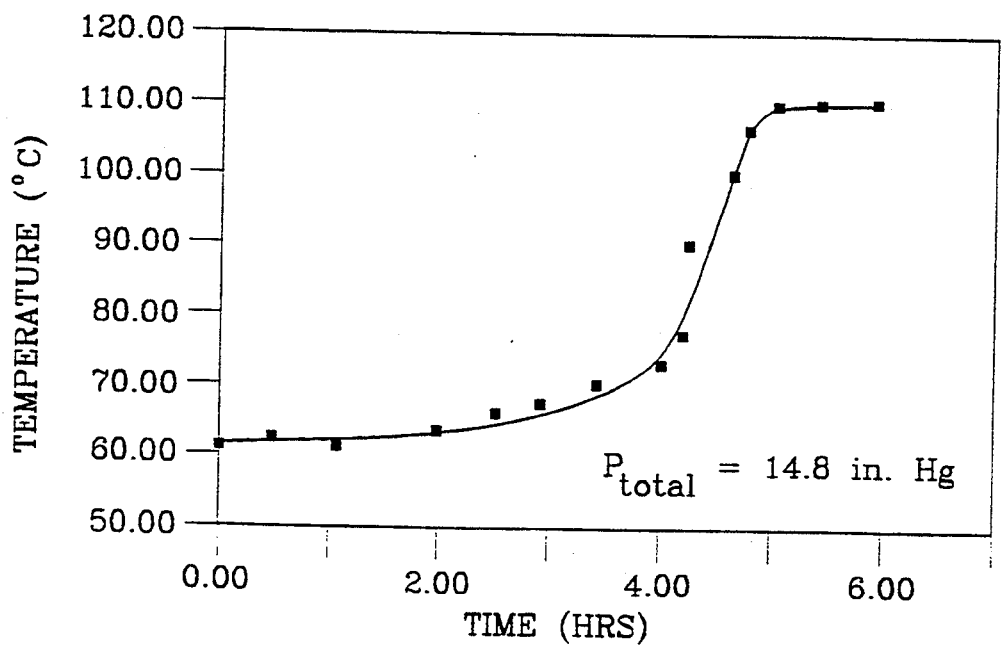
FIG. 8 is a time/temperature curve for the dewatering/decomposition experiment described in FIG. 7.

FIG. 7 shows the rates of water and TMA removal from an aqueous solution initially containing 2.0 moles TMA/mole succinic acid. FIG. 8 shows the corresponding solution temperature, which initially corresponds to the rising boiling point of the solution. At the end of the run, the temperature is held constant at 112° C.

Despite its volatility, TMA is initially held in solution due to complexation by the acid. The trimethylammonium carboxylate is decomposed when a high enough temperature is reached and/or as crystallization of the acid occurs, driving the decomposition reaction. TMA is released after most of the water has been removed. The extra release of TMA at the start of the run resulted from a slight excess of TMA in the initial aqueous solution.

Similar experiments were carried out with aqueous solutions of the di-trimethylammonium salt of fumaric acid. As with succinic acid, the TMA is released after most of the water is removed, and again an end-product containing the acid in crystalline form is obtained.

EXAMPLES 4 AND 5

The following is a general procedure which was followed in studies carried out using a solid acid-sorbing phase.

Loading of Resin with Acid

Resin samples were loaded with succinic acid using the following procedure. One-gram samples of resin were contacted with approximately 10 ml of 6% by weight succinic acid in a 20-ml scintillation vial. The two phases were equilibrated for at least 48 hours on a shaker bath thermostatted at 25° C. The phases were then separated by centribugation for 8 minutes at 2000 rpm, and the resin was weighed. The concentrations of acid in the initial and final solutions were determined by titration to pH 8.7 with sodium hydroxide. The amount of acid on the loaded resin was then determined through a mass balance.

Leaching Experiments

Each 1-g resin sample was contacted with 13 ml aqueous trimethylamine (TMA) in a scintillation vial. The two phases were again equilibrated for 48 hours on a shaker bath at 25° C. The phases were then separated by centrifugation and the resin weighed. The concentration of TMA in the initial solution was determined by adding a sample to an excess of 1N hydrochloric acid, then titrating to pH 5.0 with sodium hydroxide. The concentration of acid in the aqueous phase was obtained by HPLC analysis using a C18 column. The concentration of acid remaining on the sorbent was determined by leaching the resin with 1N hydrochloric acid, then analyzing the leachate by HPLC. A mass balance on the acid closed within the experimental error.

Results of Leachings using the Procedures

Figure 9:
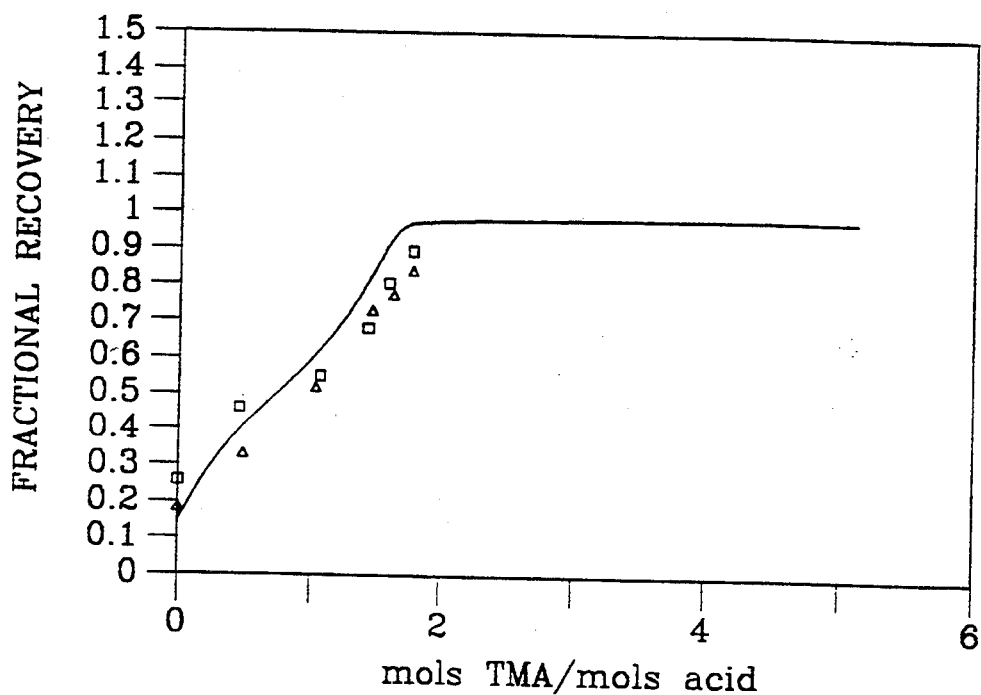
FIG. 9 is a graph illustrating the recovery possible using the process of the invention to leach succinic acid from AG3-X4 solid absorbent.
Figure 10:
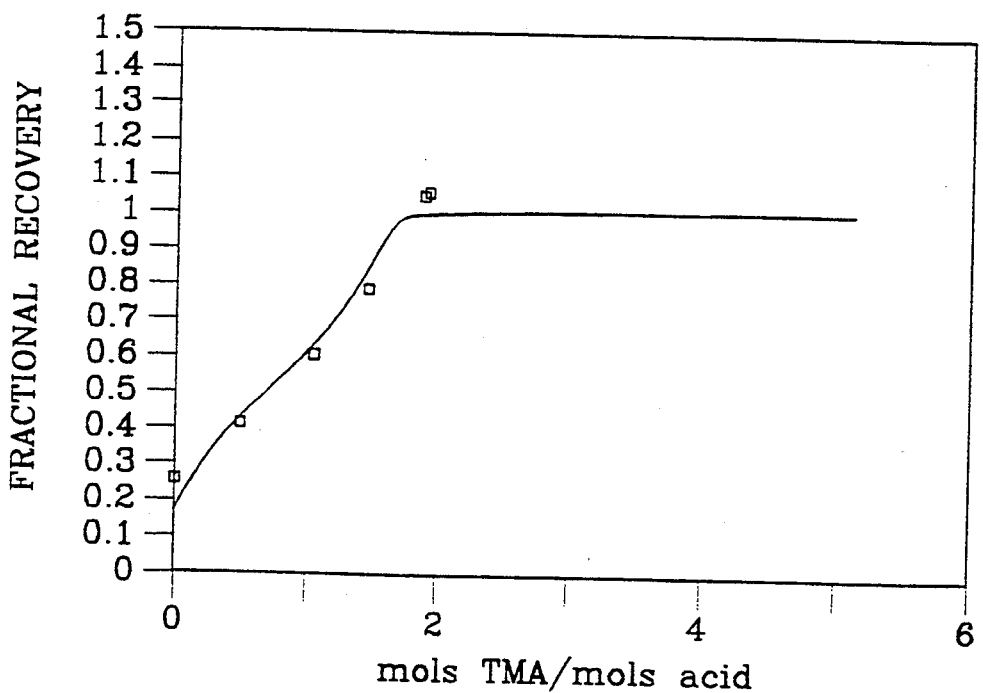
FIG. 10 is a graph illustrating the recovery possible using the process of the invention to leach succinic acid from MWA-1 solid adsorbent.

Results for the leaching of succinic acid from two different adsorbents, Bio-Rad AG3-X4 and Dowex MWA-1, are shown in FIGS. 9 and 10. For MWA-1, essentially 100% of the acid was leached into the aqueous phase at conditions in which the molar ratio of TMA to acid was at least 2:1. For AG3-X4, a recovery of 87% of the acid was achieved at a 2:1 molar ratio. The curves shown ar theoretical curves generated from the chemical-equilibrium and mass-balance equations that describe the system. The data fit to these curves.

Regeneration

The leach liquid generated above contained trimethylammoniumsuccinate. The liquid can be dewatered and decomposed to form succinic acid which is recovered and trimethylamine which is recycled.

What is claimed is:

1. A process for recovering carboxylic acid from a carboxylic acid-containing aqueous feedstream comprising:
   (a) contacting the carboxylic acid-containing feedstream with an acid-sorbing phase under conditions whereby carboxylic acid is sorbed from the feedstream to the acid-sorbing phase, thereby forming an acid-depleted aqueous feedstream and an acid-enriched acid-sorbing phase;
   (b) separating the acid-depleted aqueous feedstream from the acid-enriched acid sorbing phase;
   (c) contacting the separated acid-sorbing phase with an aqueous solution of low molecular weight alkylamine, thereby solubilizing said carboxylic acid from the sorbing phase into said aqueous solution as alkylammonium carboxylate, and forming a carboxylic-acid lean acid-sorbing phase;
   (d) separating the aqueous solution of alkylammonium carboxylate from the acid-lean acid-sorbing phase;
   (e) treating the aqueous solution of alkylammonium carboxylate to decompose the alkylammonium carboxylate to yield the carboxylic acid and the alkylamine; and
   (f) recovering the carboxylic acid yielded in step (e).

2. The process of claim 1 wherein in step (c) the alkylamine is a trialkylamine.

3. The process of claim 2 wherein the trialkylamine is trimethylamine.

4. The process of claim 1 wherein in step (e) said treating comprises dewatering and removing the alkylamine.

5. A process for regenerating a carboxylic acid-laden carboxylic acid sorbent phase comprising:
   (a) contacting the carboxylic acid-laden sorbent phase with an aqueous solution of low molecular weight alkylamine, thereby extracting said carboxylic acid from the sorbent phase into said aqueous solution as alkylammonium carboxylate, and forming a carboxylic-acid lean regenerated sorbent phase;
   (b) separating the aqueous solution of alkylammonium carboxylate from the acid-lean regenerated sorbent phase;
   (c) treating the aqueous solution of alkylammonium carboxylate to decompose the alkylammonium carboxylate to yield the carboxylic acid and the alkylamine; and
   (d) recovering the carboxylic acid yielded in step (c).

6. The process of claim 5 wherein, in step (a), the alkylamine is a trialkylamine.

7. The process of claim 6 wherein the trialkylamine is trimethylamine.

8. The process of claim 5 wherein, in step (c), said treating compresses dewatering and removing the alkylamine.

9. A process for recovering carboxylic acid from a carboxylic acid-containing aqueous feedstream comprising:
   (a) contacting the carboxylic acid-containing feedstream with a liquid organic extraction acid-sorbing phase under conditions whereby carboxylic acid is sorbed from the feedstream to the acid-sorbing phase, thereby forming an acid-depleted aqueous feedstream and an acid-enriched acid-sorbing phase;
   (b) separating the acid-depleted aqueous feedstream from the acid-enriched acid-sorbing phase;
   (c) contacting the separated liquid acid-sorbing phase with an aqueous solution of low molecular weight alkylamine, thereby solubilizing said carboxylic acid from the liquid sorbing phase into said aqueous solution as alkylammonium carboxylate, and forming a carboxylic-acid lean acid-sorbing phase;
   (d) separating the aqueous solution of alkylammonium carboxylate from the acid-lean liquid acid-sorbing phase;
   (e) treating the aqueous solution of alkylammonium carboxylate to decompose the alkylammonium carboxylate to yield the carboxylic acid and the alkylamine; and
   (f) recovering the carboxylic acid yielded in step (e).

10. The process of claim 9 wherein in step (c) the alkylamine is a trialkylamine.

11. The process of claim 10 wherein the trialkylamine is trimethylamine.

12. The process of claim 9 wherein in step (e) said treating comprises dewatering and removing the alkylamine.

13. A process for regenerating a carboxylic acid-laden liquid organic extraction carboxylic acid sorbent phase comprising:
   (a) contacting the carboxylic acid-laden organic liquid extraction sorbent phase with an aqueous solution of low molecular weight alkylamine, thereby solubilizing said carboxylic acid from the sorbent phase into said aqueous solution as alkylammonium carboxylate, and forming a carboxylic-acid lean regenerated sorbent phase;
   (b) separating the aqueous solution of alkylammonium carboxylate from the acid-lean regenerated sorbent phase;
   (c) treating the aqueous solution of alkylammonium carboxylate to decompose the alkylammonium carboxylate to yield the carboxylic acid and the alkylamine; and
   (d) recovering the carboxylic acid yielded in step (c).

14. The process of claim 13 wherein, in step (a), the alkylamine is a trialkylamine.

15. The process of claim 14 wherein the trialkylamine is trimethylamine.

16. The process of claim 15 wherein, in step (c), said treating compresses dewatering and removing the alkylamine.

17. A process for regenerating a carboxylic acid-laden carboxylic acid solid sorbent phase comprising:
   (a) contacting the carboxylic acid-laden sorbent phase with an aqueous solution of low molecular weight alkylamine, thereby solubilizing said carboxylic acid from the sorbent phase into said aqueous solution as alkylammonium carboxylate, and forming a carboxylic-acid lean regenerated sorbent phase;
   (b) separating the aqueous solution of alkylammonium carboxylate from the acid-lean regenerated sorbent phase;
   (c) treating the aqueous solution of alkylammonium carboxylate to decompose the alkylammonium carboxylate to yield the carboxylic acid and the alkylamine; and
   (d) recovering the carboxylic acid yielded in step (c).

18. The process of claim 17 wherein, in step (a), the alkylamine is a trialkylamine.

19. The process of claim 18 wherein the trialkylamine is trimethylamine.

20. The process of claim 17 wherein, in step (c), said treating comprises dewatering and removing the alkylamine.

21. A process for recovering carboxylic acid from a carboxylic acid-containing aqueous feedstream comprising:
   (a) contacting the carboxylic acid-containing feedstream with an acid-sorbing solid adsorbent phase under conditions whereby carboxylic acid is sorbed from the feedstream to the acid-sorbing phase, thereby forming an acid-depleted aqueous feedstream and an acid-enriched acid-sorbing phase;
   (b) separating the acid-depleted aqueous feedstream from the acid-enriched acid sorbing phase;
   (c) contacting the separated acid-sorbing phase with an aqueous solution of low molecular weight alkylamine, thereby solubilizing said carboxylic acid from the sorbing phase into said aqueous solution as alkylammonium carboxylate, and forming a carboxylic-acid lean acid-sorbing phase;
   (d) separating the aqueous solution of alkylammonium carboxylate from the acid-lean acid-sorbing phase;
   (e) treating the aqueous solution of alkylammonium carboxylate to decompose the alkylammonium carboxylate to yield the carboxylic acid and the alkylamine; and
   (f) recovering the carboxylic acid yielded in step (e).

22. The process of claim 21 wherein in step (c) the alkylamine is a trialkylamine.

23. The process of claim 22 wherein the trialkylamine is trimethylamine.

24. The process of claim 23 wherein in step (e) said treating comprises dewatering and removing the alkylamine.

* * * * *